(12) United States Patent
Yazdan Panah et al.

(10) Patent No.: US 11,248,223 B2
(45) Date of Patent: Feb. 15, 2022

(54) METHOD OF RNA IN VITRO TRANSCRIPTION USING A BUFFER CONTAINING A DICARBOXYLIC ACID OR TRICARBOXYLIC ACID OR A SALT THEREOF

(71) Applicant: CureVac AG, Tübingen (DE)

(72) Inventors: Benyamin Yazdan Panah, Tübingen (DE); Aniela Wochner, Tübingen (DE); Tilmann Roos, Kusterdingen (DE); Andreas Funkner, Tübingen (DE); Martin Kunze, Rottenburg (DE)

(73) Assignee: CureVac AG, Tübingen (DE)

( * ) Notice: Subject to any disclaimer, the term of this patent is extended or adjusted under 35 U.S.C. 154(b) by 607 days.

(21) Appl. No.: 16/012,751

(22) PCT Filed: Dec. 23, 2016

(86) PCT No.: PCT/EP2016/082534
§ 371 (c)(1),
(2) Date: Jun. 19, 2018

(87) PCT Pub. No.: WO2017/109161
PCT Pub. Date: Jun. 29, 2017

(65) Prior Publication Data
US 2019/0010485 A1    Jan. 10, 2019

(30) Foreign Application Priority Data
Dec. 23, 2015    (WO) .................. PCT/EP2015/081175

(51) Int. Cl.
*C12N 15/10*    (2006.01)
*C12P 19/34*    (2006.01)
*C12Q 1/6844*    (2018.01)

(52) U.S. Cl.
CPC .............. *C12N 15/10* (2013.01); *C12P 19/34* (2013.01); *C12Q 1/6844* (2013.01)

(58) Field of Classification Search
CPC .................................. C12N 15/10; C12P 19/34
See application file for complete search history.

(56) References Cited

U.S. PATENT DOCUMENTS

| 5,849,546 A | 12/1998 | Sousa |
| 6,261,773 B1 * | 7/2001 | Segawa ................ C12Q 1/6848 435/6.12 |

(Continued)

FOREIGN PATENT DOCUMENTS

| WO | WO 1995/008626 | 3/1995 |
| WO | WO 2008/016473 | 2/2008 |

(Continued)

OTHER PUBLICATIONS

Taverniti (Nucleic Acids Research, 2015, 43(1):482-492) (Year: 2015).*

(Continued)

*Primary Examiner* — Jeremy C Flinders
(74) *Attorney, Agent, or Firm* — Parker Highlander PLLC

(57) ABSTRACT

The present invention relates to a buffer system comprising a dicarboxylic acid or tricarboxylic acid or a salt thereof for synthesizing RNA molecules as well as a method of RNA in vitro transcription using this buffer system. The present invention also provides the use of this buffer system in RNA in vitro transcription and in the reduction or prevention of precipitates during RNA in vitro transcription.

29 Claims, 5 Drawing Sheets

Specification includes a Sequence Listing.

(56) References Cited

U.S. PATENT DOCUMENTS

| | | | |
|---|---|---|---|
| 7,074,596 B2 | 7/2006 | Darzynkiewicz et al. | |
| 2002/0177570 A1* | 11/2002 | Milburn | C12P 19/34 514/44 R |
| 2005/0032730 A1 | 2/2005 | von der Mülbe et al. | |
| 2005/0059624 A1 | 3/2005 | Hoerr et al. | |
| 2005/0250723 A1 | 11/2005 | Hoerr et al. | |
| 2006/0134739 A1 | 6/2006 | Chatterjee | |
| 2006/0188490 A1 | 8/2006 | Hoerr et al. | |
| 2008/0003602 A1* | 1/2008 | Nelson | C12Q 1/6865 435/6.18 |
| 2008/0025944 A1 | 1/2008 | Hoerr et al. | |
| 2008/0267873 A1 | 10/2008 | Hoerr et al. | |
| 2009/0324584 A1 | 12/2009 | Hoerr et al. | |
| 2010/0048883 A1 | 2/2010 | Ketterer et al. | |
| 2010/0189729 A1 | 7/2010 | Hoerr et al. | |
| 2010/0203076 A1 | 8/2010 | Fotin-Mleczek et al. | |
| 2010/0291156 A1 | 11/2010 | Barner et al. | |
| 2010/0305196 A1 | 12/2010 | Probst et al. | |
| 2011/0053829 A1 | 3/2011 | Baumhof et al. | |
| 2011/0250225 A1 | 10/2011 | Fotin-Mleczek et al. | |
| 2012/0021043 A1 | 1/2012 | Kramps et al. | |
| 2012/0258046 A1 | 10/2012 | Mutzke | |
| 2013/0129754 A1 | 5/2013 | Thess et al. | |
| 2013/0142818 A1 | 6/2013 | Baumhof et al. | |
| 2013/0259879 A1 | 10/2013 | Baumhof et al. | |
| 2013/0280283 A1 | 10/2013 | Lorenz et al. | |
| 2013/0295043 A1 | 11/2013 | Kallen et al. | |
| 2013/0336998 A1 | 12/2013 | Kallen et al. | |
| 2015/0037326 A1 | 2/2015 | Butler-Ransohoff et al. | |
| 2015/0050302 A1 | 2/2015 | Thess | |
| 2015/0057340 A1 | 2/2015 | Thess et al. | |
| 2015/0093413 A1 | 4/2015 | Thess et al. | |
| 2015/0118183 A1 | 4/2015 | Baumhof | |
| 2015/0118264 A1 | 4/2015 | Baumhof et al. | |
| 2015/0165006 A1 | 6/2015 | Thess et al. | |
| 2015/0184195 A1 | 7/2015 | Thess | |
| 2015/0218554 A1 | 8/2015 | Thess | |
| 2015/0306249 A1 | 10/2015 | Baumhof et al. | |
| 2015/0320847 A1 | 11/2015 | Thess et al. | |
| 2016/0130345 A1 | 5/2016 | Fotin-Mleczek et al. | |
| 2016/0166668 A1 | 6/2016 | Kallen et al. | |
| 2016/0166678 A1 | 6/2016 | Kallen et al. | |
| 2016/0166710 A1 | 6/2016 | Baumhof | |
| 2016/0166711 A1 | 6/2016 | Schnee et al. | |
| 2016/0168207 A1 | 6/2016 | Kramps et al. | |
| 2016/0168227 A1 | 6/2016 | Kallen et al. | |
| 2016/0235864 A1 | 8/2016 | Schlake | |
| 2016/0304883 A1 | 10/2016 | Grund | |
| 2016/0304938 A1 | 10/2016 | Wochner | |
| 2016/0326575 A1 | 11/2016 | von der Mülbe | |
| 2016/0331844 A1 | 11/2016 | Fotin-Mleczek et al. | |
| 2017/0014496 A1 | 1/2017 | Fotin-Mleczek et al. | |
| 2017/0029847 A1 | 2/2017 | Thess | |
| 2017/0114378 A1 | 4/2017 | Wochner et al. | |
| 2017/0252430 A1 | 9/2017 | Fotin-Mleczek | |
| 2017/0326225 A1 | 11/2017 | Rauch | |
| 2018/0044687 A1 | 2/2018 | Thess et al. | |
| 2018/0125952 A1 | 5/2018 | Fotin-Mleczek | |
| 2018/0126003 A1 | 5/2018 | Hoerr | |
| 2018/0142275 A1 | 5/2018 | Roos et al. | |
| 2018/0147146 A1 | 5/2018 | Eber et al. | |
| 2018/0148727 A1 | 5/2018 | Grund | |
| 2018/0201967 A1 | 7/2018 | Eber et al. | |
| 2018/0208957 A1 | 7/2018 | Roos et al. | |
| 2018/0214537 A1 | 8/2018 | Mutzke et al. | |
| 2018/0237786 A1 | 8/2018 | Schlake | |
| 2018/0237817 A1 | 8/2018 | Roos et al. | |
| 2018/0243219 A1 | 8/2018 | Ketterer et al. | |
| 2018/0296663 A1 | 10/2018 | Hipp et al. | |
| 2018/0298372 A1 | 10/2018 | Funkner et al. | |
| 2018/0312545 A1 | 11/2018 | Baumhof et al. | |
| 2018/0371392 A1 | 12/2018 | Mayer | |
| 2019/0017100 A1 | 1/2019 | Wochner | |
| 2019/0024096 A1 | 1/2019 | Schmid et al. | |
| 2019/0040378 A1 | 2/2019 | Fotin-Mleczek et al. | |
| 2019/0049414 A1 | 2/2019 | Wochner et al. | |
| 2019/0083602 A1 | 3/2019 | Roos et al. | |
| 2019/0100784 A1 | 4/2019 | Eber et al. | |
| 2019/0125857 A1 | 5/2019 | Rauch et al. | |
| 2019/0133950 A1 | 5/2019 | Eber et al. | |

FOREIGN PATENT DOCUMENTS

| | | |
|---|---|---|
| WO | WO 2008/077592 | 7/2008 |
| WO | WO 2008/157688 | 12/2008 |
| WO | WO 2009/149253 | 12/2009 |
| WO | WO 2011/015347 | 2/2011 |
| WO | WO 2013/052523 | 4/2013 |
| WO | WO 2015/188933 | 12/2015 |
| WO | WO 2016/193206 | 12/2016 |
| WO | WO 2017/021546 | 2/2017 |
| WO | WO 2017/025447 | 2/2017 |
| WO | WO 2017/064146 | 4/2017 |
| WO | WO 2017/081110 | 5/2017 |
| WO | WO 2017/137095 | 8/2017 |
| WO | WO 2017/140905 | 8/2017 |
| WO | WO 2017/162297 | 9/2017 |
| WO | WO 2017/182634 | 10/2017 |
| WO | WO 2017/186928 | 11/2017 |
| WO | WO 2017/191258 | 11/2017 |
| WO | WO 2017/191274 | 11/2017 |
| WO | WO 2017/203008 | 11/2017 |
| WO | WO 2017/212006 | 12/2017 |
| WO | WO 2017/212007 | 12/2017 |
| WO | WO 2017/212008 | 12/2017 |
| WO | WO 2017/212009 | 12/2017 |
| WO | WO 2018/033254 | 2/2018 |
| WO | WO 2018/078053 | 5/2018 |

OTHER PUBLICATIONS

Rodgers (RNA, 2002, 8(12):1526-1537) (Year: 2002).*

Brunelle et al., "In vitro transcription from plasmid or PCR-amplified DNA," *Methods Enzymol.*, 530:101-114, 2013.

Forconi et al., "Metal ion-based RNA cleavage as a structural probe," *Methods Enzymol.*, 468:91-106, 2009.

Fotin-Mleczek et al., "Highly potent mRNA-based cancer vaccines represent an attractive platform for combination therapies supporting an improved therapeutic effect," *J. Gene Med.*, 14(6):428-439, 2012.

Geall et al., "RNA: the new revolution in nucleic acid vaccines," *Semin. Immunol.*, 25(2):152-159, 2013.

International Preliminary Report on Patentability issued in corresponding PCT Application No. PCT/EP2016/082534, dated Jun. 26, 2018.

International Search Report and Written Opinion issued in corresponding PCT Application No. PCT/EP2016/082534, dated May 31, 2017.

Kern et al., "Application of a fed-batch system to produce RNA by in vitro transcription," *Biotechnol. Prog.*, 15:174-184, 1999.

Kern et al., "Application of Solution Equilibrium Analysis to inVitro RNA Transcription," *Biotechnol. Prog.*, 13:747-756, 1997.

Kore et al., "Synthesis and biological validation of N7-(4-chlorophenoxyethyl) substituted dinucleotide cap analogs for mRNA translation", *Bioorg. Med. Chem.*, 21(15):4570-4574, 2013.

Toffano et al., "Purification of an endogenous protein inhibitor of the high affinity binding of gamma-aminobutyric acid to synaptic membranes of rat brain," *PNAS*, 75(8):4024-4028, 1978.

Tran et al., "Mechanism of poly (A) signal transduction to RNA polymerase II in vitro," *Mol. Cell. Biol.*, 21(21):7495-7508, 2001.

* cited by examiner ic acid (HEPES) and tris(hydroxymethyl)aminomethane (Tris). The pH value of the buffer is commonly adjusted to a pH value of 6 to 8.5. Some commonly used transcription buffers comprise 80 mM HEPES/KOH, pH 7.5 and 40 mM Tris/HCl, pH 7.5.

METHOD OF RNA IN VITRO TRANSCRIPTION USING A BUFFER CONTAINING A DICARBOXYLIC ACID OR TRICARBOXYLIC ACID OR A SALT THEREOF

This application is a national phase application under 35 U.S.C. § 371 of International Application No. PCT/EP2016/082534, filed Dec. 23, 2016, which claims benefit of International Application No. PCT/EP2015/081175, filed Dec. 23, 2015, the entire contents of each of which are hereby incorporated by reference.

FIELD OF THE INVENTION

The present invention relates to a buffer system comprising a dicarboxylic acid or tricarboxylic acid or a salt thereof for synthesizing RNA molecules as well as a method of RNA in vitro transcription using this buffer system. The present invention also provides the use of this buffer system in an RNA in vitro transcription process and in the reduction or prevention of precipitates during RNA in vitro transcription.

INTRODUCTION

Therapeutic ribonucleic acid (RNA) molecules represent an emerging class of drugs. RNA-based therapeutics include mRNA molecules encoding antigens for use as vaccines (Fotin-Mleczek et al. (2012) J. Gene Med. 14(6):428-439). In addition, it is envisioned to use RNA molecules for replacement therapies, e.g. providing missing proteins such as growth factors or enzymes to patients. Furthermore, the therapeutic use of non-coding immunostimulatory RNA molecules and other non-coding RNAs such as microRNAs, siRNAs, CRISPR/Cas9 guide RNAs, and long non-coding RNAs is considered.

For the successful development of RNA therapeutics, the production of RNA molecules as active pharmaceutical ingredients must be efficient in terms of yield, quality, safety and costs, especially when RNA is produced at a large scale.

In the art, straight-forward processes for the recombinant production of RNA molecules in preparative amounts have been developed in a process called "RNA in vitro transcription". The term "RNA in vitro transcription" relates to a process wherein RNA is synthesized in a cell-free system (in vitro). RNA is commonly obtained by enzymatic DNA dependent in vitro transcription of an appropriate DNA template, which is often a linearized plasmid DNA template. The promoter for controlling RNA in vitro transcription can be any promoter for any DNA dependent RNA polymerase. Particular examples of DNA dependent RNA polymerases are the bacteriophage enzymes T7, T3, and SP6 RNA polymerases.

Methods for RNA in vitro transcription are known in the art (see for example Geall et al. (2013) Semin. Immunol. 25(2): 152-159; Brunelle et al. (2013) Methods Enzymol. 530: 101-14). Reagents used in said methods may include: a linear DNA template with a promoter sequence that has a high binding affinity for its respective RNA polymerase; ribonucleoside triphosphates (NTPs) for the four bases (adenine, cytosine, guanine and uracil); a cap analog (e.g., m7G(5')ppp(5')G (m7G)); other modified nucleotides; DNA-dependent RNA polymerase (e.g., T7, T3 or SP6 RNA polymerase); ribonuclease (RNase) inhibitor to inactivate any contaminating RNase; pyrophosphatase to degrade pyrophosphate, which inhibits transcription; MgCl$_2$, which supplies Mg$^{2+}$ as a cofactor for the RNA polymerase; antioxidants (e.g. DTT); polyamines such as spermidine; and a buffer to maintain a suitable pH value.

Common buffer systems used in RNA in vitro transcription include 4-(2-hydroxy-ethyl)-1-piperazineethanesulfonic acid (HEPES) and tris(hydroxymethyl)aminomethane (Tris). The pH value of the buffer is commonly adjusted to a pH value of 6 to 8.5. Some commonly used transcription buffers comprise 80 mM HEPES/KOH, pH 7.5 and 40 mM Tris/HCl, pH 7.5.

The transcription buffer also contains a magnesium salt such as MgCl$_2$ commonly in a range between 5-50 mM. Magnesium ions (Mg$^{2+}$) are an essential component in an RNA in vitro transcription buffer system because free Mg$^{2+}$ acts as cofactor in the catalytic center of the RNA polymerase and is critical for the RNA polymerization reaction. In diffuse binding, fully hydrated Mg ions also interact with the RNA product via nonspecific long-range electrostatic interactions.

RNA in vitro transcription reactions are typically performed as batch reactions in which all components are combined and then incubated to allow the synthesis of RNA molecules until the reaction terminates. In addition, fed-batch reactions were developed to increase the efficiency of the RNA in vitro transcription reaction (Kern et al. (1997) Biotechnol. Prog. 13: 747-756; Kern et al. (1999) Biotechnol. Prog. 15: 174-184). In a fed-batch system, all components are combined, but then additional amounts of some of the reagents are added over time (e.g., NTPs, MgCl$_2$) to maintain constant reaction conditions.

Moreover, the use of a bioreactor (transcription reactor) for the synthesis of RNA molecules by in vitro transcription has been reported (WO 95/08626). The bioreactor is configured such that reactants are delivered via a feed line to the reactor core and RNA products are removed by passing through an ultrafiltration membrane (having a nominal molecular weight cut-off, e.g., 100,000 daltons) to the exit stream.

Problem in the Art

As discussed above, magnesium ions (Mg$^{2+}$) are an essential component in an RNA in vitro transcription buffer system because free Mg$^{2+}$ acts as cofactor in the catalytic center of the RNA polymerase and is therefore critical for the RNA polymerization reaction. Conventional buffer systems for RNA in vitro transcription (e.g., HEPES buffer, Tris-HCl buffer) contain high concentrations of free magnesium ions, because free Mg$^{2+}$ ions are required to guarantee a high activity of the RNA polymerase enzyme. However the free Mg$^{2+}$ ions present in buffer systems known in the art can cause dramatic problems, especially in the context of high-yield/industrial-scale RNA production. Some of the major problems associated with free Mg$^{2+}$ ions in the production of RNA are outlined below.

First, the binding of magnesium to RNA can cause integrity problems, because Mg$^{2+}$ ions can catalyze self-cleavage of the RNA product, leading to undesired abortive sequences (Forconi, Marcello, and Daniel Herschlag (2009) Methods in enzymology 468: 91-106).

Second, during RNA in vitro transcription, the enzymatic polymerization reaction generates one mole pyrophosphate per mole incorporated nucleotide triphosphate (NTP): $(NMP)_n + NTP \rightarrow (NMP)_{n+1} + PP_i$. The pyrophosphate ($PP_i$) is then cleaved into two moles ortho phosphate by the enzyme pyrophosphatase ($P_2O_7^{4-} + H_2O \rightarrow 2HPO_4^{2-}$). However, the hydrolysis of PPi to Pi during the running reaction is not sufficient to overcome turbidity of the reaction as widely believed in the art. Free magnesium and phosphate ions result in the precipitation of magnesium phosphate salts, too (e.g., $Mg(H_2PO_4)_2$; $MgHPO_4$; $Mg_3(PO_4)_2$). In addition to that, hydrated magnesium ions interact with the RNA product via nonspecific long-range electrostatic interactions, which may lead to a magnesium-driven precipitation of the RNA product.

The generation of magnesium-driven precipitates as outlined above can cause major problems in the production process of RNA, especially in large-scale/industrial-scale RNA production:

First of all, precipitations as described above will have an impact on RNA production costs because RNA product, DNA template, enzyme (RNA polymerase, pyrophosphatase, RNAse inhibitors) and raw materials (NTPs, cap analog) may co-precipitate with magnesium-dependent precipitates.

Next, precipitation introduces uncontrolled changes in the reaction conditions (e.g., NTP concentration, enzyme concentration, buffer conditions), which has to be avoided in a robust process applicable for industrial RNA production.

Magnesium-driven precipitation may lead to a drop in the free $Mg^{2+}$ concentration, resulting in depletion of magnesium ions from the RNA polymerase reaction center. A consequence of that would be a less efficient RNA in vitro transcription.

In addition, uncontrolled reaction conditions, caused by the magnesium-driven precipitation, are highly problematic in the context of feeding strategies, because the feeding of raw materials (e.g., NTPs) cannot be precisely calculated and adjusted any more. In addition to that, in the context of continuous RNA production processes, an accumulation of precipitate over time may occur, which can eventually lead to a stop of the production process.

Quantification of nucleotides is commonly performed using UV-light spectrometry. In a RNA transcription reaction it is beneficial to quantify free NTPs using spectrometry. With such a measurement, the progress of RNA in vitro transcription can be calculated because the decrease of free NTPs can be translated back into the produced RNA molecules. Such a measurement is technically applicable in settings where the transcription buffer (containing NTPs) is separated from the RNA product and the DNA template (e.g., via a low molecular weight cutoff membrane). In such a setting, magnesium-driven precipitation would cause a turbidity of the buffer solution and that, in consequence, would impair spectrometric quantification of NTPs.

Moreover, precipitation as described above may cause general procedural problems because e.g., filtration membranes, tubing systems and other elements of a transcription setting (e.g., transcription reactor) may be clogged by the precipitates.

Magnesium-driven precipitates may also cause problems during the purification procedure of the RNA product. For example, a direct purification of the RNA product from the RNA in vitro transcription reaction by methods such as tangential flow filtration may be largely impeded by precipitates.

Finally, a depletion of ions caused by precipitations may cause further problems downstream of the RNA in vitro transcription reaction, because the hydrolysis of the DNA template via DNAses (which conventionally happens in the IVT buffer after addition of $CaCl_2$) may be impeded which may eventually lead to DNA contaminations in the final RNA product.

In view of the above described problems, there is a continued need for improved conditions for the RNA in vitro transcription reaction, especially in the establishment of robust large-scale RNA production settings. Therefore, preventing magnesium-driven precipitation as described above would be a major advantage in the art, and would improve the establishment of a robust and cost-effective industrial RNA production process.

Solution of the Problem and Description of the Invention

The problems outlined above are solved by the subject-matter of the present invention.

In an initial experiment, the inventors characterized the precipitates formed during enzymatic RNA in vitro transcription using a state-of-the-art HEPES buffer. They could show that magnesium-driven precipitates contain RNA and proteins (e.g., RNA polymerase, RNAse Inhibitor) (see FIG. 1).

In a next set of experiments, the inventors showed that the use of Tris-citrate buffer surprisingly prevents the formation of precipitates (Tris pH 7.5; 24 mM citric acid) in the process of RNA in vitro transcription. The effect was not observed with another organic acid such as acetate (see FIG. 2).

To further characterize the effect of citrate on the prevention of precipitation, an experiment was conducted where different concentrations of citrate (in a Tris buffer, pH 8.0) were used in an RNA in vitro transcription experiment, ranging from 0-25 mM citrate. The results showed that the reduction of precipitations was a dose-dependent effect of citrate. Moreover, the experiment showed that at citrate concentrations >10 mM, the formation of precipitates was already strongly reduced, and at concentrations >15 mM, the formation of precipitates could be prevented (see FIG. 3).

To characterize whether the effect of citrate observed for Tris buffers is also transferrable to other buffers such as HEPES, the inventors conducted an experiment where different concentrations of citrate, ranging from 0-25 mM citrate, were used in a HEPES buffer in an RNA in vitro transcription experiment. The results showed that the reduction of precipitations was a dose-dependent effect of citrate in HEPES buffer. Moreover, the experiment showed that at citrate concentrations >10 mM, the formation of precipitates could be prevented (see FIG. 4).

Finally, an experiment was conducted to investigate the effect of citrate in the RNA in vitro transcription reaction on the subsequent hydrolysis of the DNA template by adding DNase1 and calcium chloride to the RNA in vitro transcription reaction. The results showed that the use of citrate in the RNA in vitro transcription reaction promotes the hydrolysis of the DNA template (see FIG. 5).

Summarizing the above, the inventors surprisingly showed that by using a transcription buffer (Tris, HEPES) containing citrate, precipitations could be prevented during RNA in vitro transcription and the DNase-mediated hydrolysis of the DNA template could be improved.

Citrate containing buffer systems as disclosed in the present invention are broadly applicable for RNA in vitro transcription, solving the problems associated with magnesium-driven precipitations, especially in the context of industrial RNA production.

Accordingly, the present invention relates to a method for in vitro transcription of a nucleic acid template into RNA, comprising the steps of:

providing a mixture comprising a dicarboxylic or tricarboxylic acid or salt thereof, a buffer substance, ribonucleoside triphosphates, one or more magnesium salts, said nucleic acid template and RNA polymerase; and incubating the reaction mixture under suitable conditions.

The present invention also relates to a method for in vitro transcription of a nucleic acid template into RNA, comprising the steps of:

providing a mixture comprising a dicarboxylic or tricarboxylic acid or salt thereof, a buffer substance, ribonucleoside triphosphates, one or more magnesium salts, said nucleic acid template and a recombinant RNA polymerase, wherein the mixture does not comprise a proteinogenic amino acid or tRNA; and incubating the reaction mixture under suitable conditions.

Additionally, the present invention relates to a method for preparing RNA, comprising the steps of:

a) incubating a mixture comprising a dicarboxylic or tricarboxylic acid or salt thereof, a buffer substance, ribonucleoside triphosphates, one or more magnesium salts, a nucleic acid template and a recombinant RNA polymerase under suitable conditions;

b) adding a DNase to the mixture of a) and incubating the resulting mixture containing DNase under suitable conditions.

The dicarboxylic or tricarboxylic acid or salt thereof may be citric acid or a salt thereof.

In one embodiment, the concentration of citric acid or salt thereof is at least half of the concentration of magnesium ions present in the in vitro transcription reaction.

The buffer substance may be Tris base, HEPES or Tris-HCl.

In one embodiment, the concentration of the buffer substance is 10 to 100 mM.

The dicarboxylic or tricarboxylic acid or salt thereof may be used to adjust the pH of the mixture.

In one embodiment the reaction mixture comprises Tris-citrate or HEPES-KOH plus sodium citrate, ribonucleoside triphosphates, one or more magnesium salts, said nucleic acid template and RNA polymerase.

The magnesium salt may be magnesium chloride and the concentration of magnesium chloride may be 1 to 100 mM.

The reaction mixture may have a pH of 6 to 8.5 or of 7.5 to 8.0.

The RNA polymerase may be T7 RNA polymerase.

In one embodiment the total concentration of ribonucleoside triphosphates in the mixture is between 0.1 and 60 mM.

The nucleic acid template may be a linearized plasmid DNA template.

The reaction mixture may comprise one or more of ribonuclease inhibitor, pyrophosphatase, cap analog, one or more antioxidants and one or more amines and/or polyamines.

The antioxidant is DTT and the concentration of DTT may be 1 to 50 mM.

The polyamine may be spermidine and the concentration of spermidine may be 1 to 25 mM.

The method may further comprise a step (c) of purifying the RNA which may comprise HPLC using a porous reversed phase as stationary phase and/or tangential flow filtration.

In another aspect, the present invention relates to a buffer for in vitro transcription of RNA comprising a dicarboxylic or tricarboxylic acid or a salt thereof and a buffer substance.

The present invention also relates to a buffer for in vitro transcription of RNA comprising a dicarboxylic or tricarboxylic acid or a salt thereof and Tris as a buffer substance.

The dicarboxylic or tricarboxylic acid or a salt thereof may be citric acid or citrate and the concentration of citric acid or citrate may be at least 1 mM.

The buffer substance is Tris or HEPES and the buffer may be Tris-citrate or HEPES-KOH plus sodium citrate.

The buffer may have a pH of 6 to 8.5.

In another aspect, the present invention relates to a reaction mixture for in vitro transcription comprising said buffer and ribonucleoside triphosphates, one or more magnesium salts, a nucleic acid template and RNA polymerase.

The reaction mixture may further comprise one or more of ribonuclease inhibitor, pyrophosphatase, cap analog, one or more antioxidants and one or more amines and/or polyamines.

In another aspect, the present invention relates to a kit for in vitro transcription, comprising said buffer or said reaction mixture.

In another aspect, the present invention relates to a bioreactor for in vitro transcription, comprising said buffer or said reaction mixture.

In still another aspect the present invention relates to the use of a dicarboxylic or tricarboxylic acid or a salt thereof in a method of in vitro transcription of RNA.

In still another aspect the present invention relates to the use of a dicarboxylic or tricarboxylic acid or a salt thereof in the reduction or prevention of the formation of precipitates in a method of in vitro transcription.

The method of in vitro transcription may be as defined above.

In still another aspect the present invention relates to the use of a dicarboxylic or tricarboxylic acid or a salt thereof in promoting the hydrolysis of DNA by DNase.

The DNA hydrolysis may take place after RNA in vitro transcription.

In still another aspect the present invention relates to the use of betaine in the in vitro transcription of a nucleic acid template with a high percentage of guanosine and cytosine nucleotides.

The concentration of betaine may be 10 mM to 1 M.

DEFINITIONS

Figure 1:
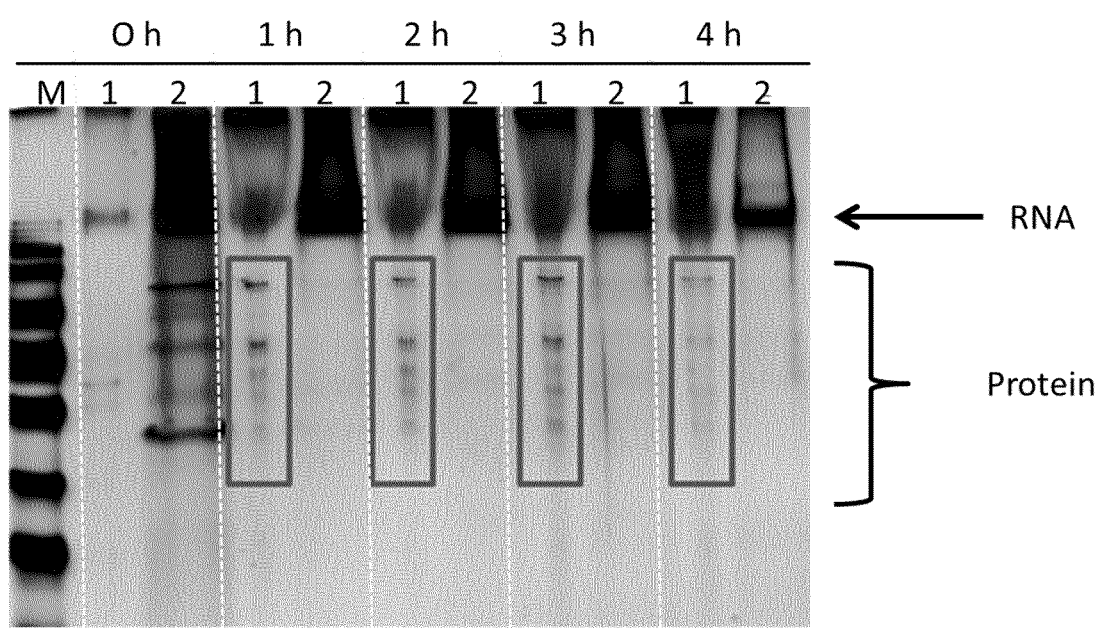
FIG. 1 shows a qualitative characterization of the precipitates formed during a HEPES buffered RNA in vitro transcription reaction. The picture shows the result of an SDS-polyacrylamide gel electrophoresis of precipitate (1) and supernatant (2) at different time points (0 h-4 h) during RNA in vitro transcription. M=marker lane. (see Example 2)

For the sake of clarity and readability the following definitions are provided. Any technical feature mentioned in these definitions may be read on each and every embodiment of the invention. Additional definitions and explanations may be specifically provided in the context of these embodiments.

In vitro transcription: The terms "in vitro transcription" or "RNA in vitro transcription" relate to a process wherein RNA is synthesized in a cell-free system (in vitro). DNA, particularly plasmid DNA, is used as template for the generation of RNA transcripts. RNA may be obtained by DNA-dependent in vitro transcription of an appropriate DNA template, which according to the present invention is preferably a linearized plasmid DNA template. The promoter for controlling in vitro transcription can be any promoter for any DNA-dependent RNA polymerase. Particular examples of DNA-dependent RNA polymerases are the T7, T3, and SP6 RNA polymerases. A DNA template for in vitro RNA transcription may be obtained by cloning of a nucleic acid, in particular cDNA corresponding to the respective RNA to be in vitro transcribed, and introducing it into an appropriate vector for in vitro transcription, for example into plasmid DNA. In a preferred embodiment of the present invention the DNA template is linearized with a suitable restriction enzyme, before it is transcribed in vitro. The cDNA may be obtained by reverse transcription of mRNA or chemical synthesis. Moreover, the DNA template for in vitro RNA synthesis may also be obtained by gene synthesis.

Methods for in vitro transcription are known in the art (Geall et al. (2013) Semin. Immunol. 25(2): 152-159; Brunelle et al. (2013) Methods Enzymol. 530:101-14). Reagents used in said method typically include:
1) a linearized DNA template with a promoter sequence that has a high binding affinity for its respective RNA polymerase such as bacteriophage-encoded RNA polymerases;
2) ribonucleoside triphosphates (NTPs) for the four bases (adenine, cytosine, guanine and uracil);
3) optionally a cap analog as defined below (e.g. m7G(5') ppp(5')G (m7G));
4) a DNA-dependent RNA polymerase capable of binding to the promoter sequence within the linearized DNA template (e.g. T7, T3 or SP6 RNA polymerase);
5) optionally a ribonuclease (RNase) inhibitor to inactivate any contaminating RNase;
6) optionally a pyrophosphatase to degrade pyrophosphate, which may inhibit transcription;
7) MgCl$_2$, which supplies Mg$^{2+}$ ions as a co-factor for the polymerase;
8) a buffer to maintain a suitable pH value, which can also contain antioxidants (e.g. DTT), amines such as betaine and/or polyamines such as spermidine at optimal concentrations.

In the method of RNA in vitro transcription according to the invention no reagents which are only required for the in vitro translation of the transcribed RNA to protein, but not for RNA in vitro transcription are used. In particular, the mixture used for RNA in vitro transcription does not contain any proteinogenic amino acid or tRNA. Further, the mixture does not contain any proteinogenic amino acid, tRNA or a cell extract containing ribosomes.

Nucleic acid: The term nucleic acid means any DNA- or RNA-molecule and is used synonymous with polynucleotide. Furthermore, modifications or derivatives of the nucleic acid as defined herein are explicitly included in the general term "nucleic acid". For example, peptide nucleic acid (PNA) is also included in the term "nucleic acid".

Nucleic acid template: The nucleic acid template provides the nucleic acid sequence which is transcribed into the RNA by the process of in vitro transcription and which therefore comprises a nucleic acid sequence which is complementary to the RNA sequence which is transcribed therefrom. In addition to the nucleic acid sequence which is transcribed into the RNA the nucleic acid template comprises a promoter to which the RNA polymerase used in the in vitro transcription process binds with high affinity.

Preferably, the nucleic acid template may be a linearized plasmid DNA template. The linear template DNA is obtained by contacting plasmid DNA with a restriction enzyme under suitable conditions so that the restriction enzyme cuts the plasmid DNA at its recognition site(s) and disrupts the circular plasmid structure. The plasmid DNA is preferably cut immediately after the end of the sequence which is to be transcribed into RNA. Hence, the linear template DNA comprises a free 5' end and a free 3' end which are not linked to each other. If the plasmid DNA contains only one recognition site for the restriction enzyme, the linear template DNA has the same number of nucleotides as the plasmid DNA. If the plasmid DNA contains more than one recognition site for the restriction enzyme, the linear template DNA has a smaller number of nucleotides than the plasmid DNA. The linear template DNA is then the fragment of the plasmid DNA which contains the elements necessary for in vitro transcription, that is a promotor element for RNA transcription and the template DNA element. The open reading frame of the linear template DNA determines the sequence of the transcribed RNA by the rules of base-pairing.

In other embodiments, the nucleic acid template may be selected from a synthetic double stranded DNA construct, a single-stranded DNA template with a double-stranded DNA region comprising the promoter to which the RNA polymerase binds, a cyclic double-stranded DNA template with promoter and terminator sequences or a linear DNA template amplified by PCR or isothermal amplification.

According to a preferred embodiment of the invention, the concentration of the nucleic acid template comprised in the in vitro transcription mixture is in a range from about 1 to 50 nM, 1 to 40 nM, 1 to 30 nM, 1 to 20 nM, or about 1 to 10 nM. Even more preferred the concentration of the nucleic acid template is from about 10 to 30 nM. Most preferred the concentration of the nucleic acid template is about 20 nM. In this context it is particularly preferred to have a concentration of the nucleic acid template of about 1 to 200 µg/ml and more preferably of about 10 to 100 µg/ml, and most preferably of about 20 to 50 µg/ml (e.g. 25 or 50 µg/ml).

RNA, mRNA: RNA is the usual abbreviation for ribonucleic acid. It is a nucleic acid molecule, i.e. a polymer consisting of nucleotide monomers. These nucleotides are usually adenosine-monophosphate (AMP), uridine-monophosphate (UMP), guanosine-monophosphate (GMP) and cytidine-monophosphate (CMP) monomers or analogs thereof, which are connected to each other along a so-called backbone. The backbone is formed by phosphodiester bonds between the sugar, i.e. ribose, of a first and a phosphate moiety of a second, adjacent monomer. The specific order of the monomers, i.e. the order of the bases linked to the sugar/phosphate-backbone, is called the RNA sequence. Usually RNA may be obtainable by transcription of a DNA sequence, e.g., inside a cell. In eukaryotic cells, transcription is typically performed inside the nucleus or the mitochondria. In vivo, transcription of DNA usually results in the so-called premature RNA which has to be processed into so-called messenger-RNA, usually abbreviated as mRNA. Processing of the premature RNA, e.g. in eukaryotic organisms, comprises a variety of different posttranscriptional-modifications such as splicing, 5'-capping, polyadenylation, export from the nucleus or the mitochondria and the like. The sum of these processes is also called maturation of RNA. The mature messenger RNA usually provides the nucleotide sequence that may be translated into an amino acid sequence of a particular peptide or protein. Typically, a mature mRNA comprises a 5'-cap, optionally a 5'UTR, an open reading frame, optionally a 3'UTR and a poly(A) sequence.

In addition to messenger RNA, several non-coding types of RNA exist which may be involved in regulation of transcription and/or translation, and immunostimulation. The term "RNA" further encompasses RNA molecules, such as viral RNA, retroviral RNA and replicon RNA, small interfering RNA (siRNA), antisense RNA, CRISPR/Cas9 guide RNA, ribozymes, aptamers, riboswitches, immunostimulating RNA, transfer RNA (tRNA), ribosomal RNA (rRNA), small nuclear RNA (snRNA), small nucleolar RNA (snoRNA), microRNA (miRNA), and Piwi-interacting RNA (piRNA).

Dicarboxylic acid or salt thereof: A dicarboxylic acid is an organic acid having two carboxyl groups (—COOH). The term includes linear saturated dicarboxylic acids having the general formula $HO_2C-(CH_2)_n-CO_2H$ such as oxalic acid, malonic acid, succinic acid, glutaric acid, adipic acid, pimelic acid, suberic acid, azelaic acid and sebacic acid. It also includes unsaturated dicarboxylic acids having at least one double bond such as maleic acid and fumaric acid as well as substituted dicarboxylic acids having at least one additional functional group such as malic acid, tartaric acid, cichoric acid and dimercaptosuccinic acid. The salt of the dicarboxylic acid comprises the dicarboxylic acid anion and a suitable cation such as $Na^+$, $K^+$, $Ca^{2+}$ or $Mg^{2+}$.

Tricarboxylic acid or salt thereof: A tricarboxylic acid is an organic acid having three carboxyl groups (—COOH). Examples of tricarboxylic acids include citric acid, isocitric acid, aconitic acid, trimesic acid, nitrilotriacetic acid and propane-1,2,3-tricarboxylic acid. In the buffer system and methods of the present invention preferably citric acid (3-carboxy-3-hydroxypentane-1,5-dioic acid) is used. The salt of the tricarboxylic acid comprises the tricarboxylic acid anion and a suitable cation such as $Na^+$, $K^+$, $Ca^{2+}$ or $Mg^{2+}$. Preferably, sodium or magnesium citrate is used. If magnesium citrate is added to the RNA in vitro transcription reaction, it is not necessary to add a magnesium salt to the reaction, since the magnesium ions within the magnesium citrate may serve as the cofactor for the RNA polymerase. Hence, in this case the reaction mixture for RNA in vitro transcription comprises magnesium citrate, a buffer substance, ribonucleoside triphosphates, a nucleic acid template and RNA polymerase.

Buffer substance: A buffer substance is a weak acid or base used to maintain the acidity (pH) of a solution near a chosen value after the addition of another acid or base. Hence, the function of a buffer substance is to prevent a rapid change in pH when acids or bases are added to the solution. Suitable buffer substances for use in the present invention are Tris (2-amino-2-hydroxymethyl-propane-1,3-diol) and HEPES (2-[4-(2-hydroxyethyl)piperazin-1-yl]ethanesulfonic acid). The buffer substance may further comprise an acid or a base for adjusting the pH, such as HCl in case of Tris (Tris-HCl) and KOH in case of HEPES (HEPES-KOH). In a preferred embodiment of the present invention citric acid is used to adjust the pH of the buffer substance, preferably of Tris base, so that no other acid has to be added. In an alternative embodiment the pH of the buffer substance is adjusted with an acid or a base such as HCl and KOH and the salt of the dicarboxylic or tricarboxylic acid, preferably citrate, is present in the reaction mixture in addition to the pH-adjusted buffer substance.

The concentration of the buffer substance within the mixture for in vitro transcription is 10 to 100 mM, 10 to 80 mM, 10 to 50 mM, 10 to 40 mM, 10 to 30 mM or 10 to 20 mM. Preferably, the concentration of the buffer substance is 80 mM.

Preferably the buffer has a pH value from 6 to 8.5, from 6.5 to 8.0, from 7.0 to 7.5, even more preferred of 7.5 or 8.0.

Ribonucleoside triphosphates: The ribonucleoside triphosphates (NTPs) GTP, ATP, CTP and UTP are the monomers which are polymerized during the in vitro transcription process. They may be provided with a monovalent or divalent cation as counterion. Preferably the monovalent cation is selected from the group consisting of $Li^+$, $Na^-$, $K^-$, $NH4^+$ or tris(hydroxymethyl)-aminomethane (Tris). Preferably, the divalent cation is selected from the group consisting of $Mg^{2+}$, $Ba^{2+}$ and $Mn^{2+}$. More preferably, the monovalent cation is $Na^+$ or tris(hydroxymethyl)-aminomethane (Tris).

According to a preferred embodiment of the invention, a part or all of at least one ribonucleoside triphosphate in the in vitro transcription reaction mixture is replaced with a modified nucleoside triphosphate as defined below.

Modified nucleoside triphosphate: The term "modified nucleoside triphosphate" as used herein refers to chemical modifications comprising backbone modifications as well as sugar modifications or base modifications. These modified nucleoside triphosphates are also termed herein as (nucleotide) analogs.

In this context, the modified nucleoside triphosphates as defined herein are nucleotide analogs/modifications, e.g. backbone modifications, sugar modifications or base modifications. A backbone modification in connection with the present invention is a modification, in which phosphates of the backbone of the nucleotides are chemically modified. A sugar modification in connection with the present invention is a chemical modification of the sugar of the nucleotides. Furthermore, a base modification in connection with the present invention is a chemical modification of the base moiety of the nucleotides. In this context nucleotide analogs or modifications are preferably selected from nucleotide analogs which are applicable for transcription and/or translation.

Sugar Modifications

The modified nucleosides and nucleotides, which may be used in the context of the present invention, can be modified in the sugar moiety. For example, the 2' hydroxyl group (OH) can be modified or replaced with a number of different "oxy" or "deoxy" substituents. Examples of "oxy"-2' hydroxyl group modifications include, but are not limited to, alkoxy or aryloxy (—OR, e.g., R=H, alkyl, cycloalkyl, aryl, aralkyl, heteroaryl or sugar); polyethyleneglycols (PEG), —O($CH_2CH_2O$)n$CH_2CH_2OR$; "locked" nucleic acids (LNA) in which the 2' hydroxyl is connected, e.g., by a methylene bridge, to the 4' carbon of the same ribose sugar; and amino groups (—O-amino, wherein the amino group, e.g., NRR, can be alkylamino, dialkylamino, heterocyclyl, arylamino, diarylamino, heteroarylamino, or diheteroaryl amino, ethylene diamine, polyamino) or aminoalkoxy.

"Deoxy" modifications include hydrogen, amino (e.g. $NH_2$; alkylamino, dialkylamino, heterocyclyl, arylamino, diaryl amino, heteroaryl amino, diheteroaryl amino, or amino acid); or the amino group can be attached to the sugar through a linker, wherein the linker comprises one or more of the atoms C, N, and O.

The sugar group can also contain one or more carbons that possess the opposite stereochemical configuration than that of the corresponding carbon in ribose. Thus, a modified nucleotide can include nucleotides containing, for instance, arabinose as the sugar.

Backbone Modifications

The phosphate backbone may further be modified in the modified nucleosides and nucleotides. The phosphate groups of the backbone can be modified by replacing one or more of the oxygen atoms with a different substituent. Further, the modified nucleosides and nucleotides can include the full replacement of an unmodified phosphate moiety with a modified phosphate as described herein. Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphate linker can also be modified by the replacement of a linking oxygen with nitrogen (bridged phosphoroamidates), sulfur (bridged phosphorothioates) and carbon (bridged methylene-phosphonates).

Base Modifications

The modified nucleosides and nucleotides, which may be used in the present invention, can further be modified in the nucleobase moiety. Examples of nucleobases found in RNA include, but are not limited to, adenine, guanine, cytosine and uracil. For example, the nucleosides and nucleotides described herein can be chemically modified on the major groove face. In some embodiments, the major groove chemical modifications can include an amino group, a thiol group, an alkyl group, or a halo group.

In particularly preferred embodiments of the present invention, the nucleotide analogs/modifications are selected from base modifications, which are preferably selected from 2-amino-6-chloropurineriboside-5'-triphosphate, 2-Aminopurine-riboside-5'-triphosphate; 2-aminoadenosine-5'-triphosphate, 2'-Amino-2'-deoxycytidine-triphosphate, 2-thiocytidine-5'-triphosphate, 2-thiouridine-5'-triphosphate, 2'-Fluorothymidine-5'-triphosphate, 2'-O-Methyl inosine-5'-triphosphate 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-Bromo-2'-deoxycytidine-5'-triphosphate, 5-Bromo-2'-deoxyuridine-5'-triphosphate, 5-iodocytidine-5'-triphosphate, 5-Iodo-2'-deoxycytidine-5'-triphosphate, 5-iodouridine-5'-triphosphate, 5-Iodo-2'-deoxyuridine-5'-triphosphate, 5-methylcytidine-5'-triphosphate, 5-methyluridine-5'-triphosphate, 5-Propynyl-2'-deoxycytidine-5'-triphosphate, 5-Propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In other embodiments, modified nucleosides include 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments, the nucleotide can be modified on the major groove face and can include replacing hydrogen on C-5 of uracil with a methyl group or a halo group.

In specific embodiments, a modified nucleoside is 5'-O-(1-Thiophosphate)-Adenosine, 5'-O-(1-Thiophosphate)-Cytidine, 5'-O-(1-Thiophosphate)-Guanosine, 5'-O-(1-Thiophosphate)-Uridine or 5'-O-(1-Thiophosphate)-Pseudouridine.

In further specific embodiments the modified nucleotides include nucleoside modifications selected from 6-aza-cytidine, 2-thio-cytidine, α-thio-cytidine, Pseudo-iso-cytidine, 5-aminoallyl-uridine, 5-iodo-uridine, N1-methyl-pseudouridine, 5,6-dihydrouridine, α-thio-uridine, 4-thio-uridine, 6-aza-uridine, 5-hydroxy-uridine, deoxy-thymidine, 5-methyl-uridine, Pyrrolo-cytidine, inosine, α-thio-guanosine, 6-methyl-guanosine, 5-methyl-cytidine, 8-oxo-guanosine, 7-deaza-guanosine, N1-methyl-adenosine, 2-amino-6-Chloro-purine, N6-methyl-2-amino-purine, Pseudo-iso-cytidine, 6-Chloro-purine, N6-methyl-adenosine, α-thio-adenosine, 8-azidoadenosine, 7-deaza-adenosine.

Further modified nucleotides have been described previously (WO 2013/052523).

Magnesium salt: A magnesium salt comprises a magnesium cation and a suitable anion such as a chloride or an acetate anion. Preferably, the magnesium salt is magnesium chloride. Preferably, the initial free $Mg^{2+}$ concentration is from about 1 to 100 mM, 1 to 75 mM, 1 to 50 mM, 1 to 25 mM, or 1 to 10 mM. Even more preferred the initial free $Mg^{2+}$ concentration is from about 10 to 30 mM or about 15 to 25 mM. Most preferred is an initial free $Mg^{2+}$ concentration of about 24 mM. The person skilled in the art will understand that the choice of the $Mg^{2+}$ concentration is influenced by the initial total NTP concentration, meaning that a higher $Mg^{2+}$ concentration has to be used, if a higher total NTP concentration is used in the in vitro transcription mixture.

RNA polymerase: The RNA polymerase is an enzyme which catalyzes the transcription of a DNA template into RNA. Suitable RNA polymerases for use in the present invention include T7, T3, SP6 and E. coli RNA polymerase. Preferably, a T7 RNA polymerase is used. Also preferably, the RNA polymerase for use in the present invention is a recombinant RNA polymerase, meaning that it is added to the RNA in vitro transcription reaction as a single component and not as part of a cell extract which contains other components in addition to the RNA polymerase. The skilled person knows that the choice of the RNA polymerase depends on the promoter present in the DNA template which has to be bound by the suitable RNA polymerase. Preferably, the concentration of the RNA polymerase is from about 1 to 100 nM, 1 to 90 nM, 1 to 80 nM, 1 to 70 nM, 1 to 60 nM, 1 to 50 nM, 1 to 40 nM, 1 to 30 nM, 1 to 20 nM, or about 1 to 10 nM. Even more preferred, the concentration of the RNA polymerase is from about 10 to 50 nM, 20 to 50 nM, or 30 to 50 nM. Most preferred is a RNA polymerase concentration of about 40 nM. In this context a concentration of 500 to 10000 U/ml of the RNA polymerase is preferred. More preferred is a concentration of 1000 to 7500 U/ml and most preferred is a concentration of 2500 to 5000 Units/ml of the RNA polymerase. The person skilled in the art will understand that the choice of the RNA polymerase concentration is influenced by the concentration of the DNA template.

Pyrophosphatase: A pyrophosphatase is an acid anhydride hydrolase that hydrolyses diphosphate bonds. In the in vitro transcription reaction it serves to hydrolyze the bonds within the diphosphate released upon incorporation of the ribonucleoside triphosphates into the nascent RNA chain. Preferably, the concentration of the pyrophosphatase is from about 1 to 20 units/ml, 1 to 15 units/ml, 1 to 10 units/ml, 1 to 5 units/ml, or 1 to 2.5 units/ml. Even more preferred the concentration of the pyrophosphatase is about 1 unit/ml or is about 5 units/ml. 5'-Cap structure: A 5' cap is typically a modified nucleotide, particularly a guanine nucleotide, added to the 5' end of an RNA molecule. Preferably, the 5' cap is added using a 5'-5'-triphosphate linkage. A 5' cap may be methylated, e.g. m7GpppN, wherein N is the terminal 5' nucleotide of the nucleic acid carrying the 5' cap, typically the 5'-end of an RNA. The naturally occurring 5' cap is m7GpppN.

Further examples of 5' cap structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3' phosphorothioate, phosphorodithioate, or bridging or non-bridging methylphosphonate moiety.

Particularly preferred 5' cap structures are CAP1 (methylation of the ribose of the adjacent nucleotide of m7G), CAP2 (methylation of the ribose of the $2^{nd}$ nucleotide downstream of the m7G), CAP3 (methylation of the ribose of the $3^{rd}$ nucleotide downstream of the m7G) and CAP4 (methylation of the ribose of the $4^{th}$ nucleotide downstream of the m7G).

A 5' cap structure may be formed by a cap analog.

Cap analog: A cap analog refers to a non-extendable di-nucleotide that has cap functionality which means that it facilitates translation or localization, and/or prevents degradation of the RNA molecule when incorporated at the 5' end of the RNA molecule. Non-extendable means that the cap analog will be incorporated only at the 5' terminus because it does not have a 5' triphosphate and therefore cannot be extended in the 3' direction by a template-dependent RNA polymerase.

Cap analogs include, but are not limited to, a chemical structure selected from the group consisting of m7GpppG, m7GpppA, m7GpppC; unmethylated cap analogs (e.g., GpppG); dimethylated cap analog (e.g., m2,7GpppG), trimethylated cap analog (e.g., m2,2,7GpppG), dimethylated symmetrical cap analogs (e.g., m7Gpppm7G), or anti reverse cap analogs (e.g., ARCA; m7,2'OmeGpppG, m7,2'dGpppG, m7,3'OmeGpppG, m7,3'dGpppG and their tetraphosphate derivatives) (Stepinski et al., 2001. RNA 7(10):1486-95). Examples of cap analogs are shown in Table 1.

TABLE 1

Cap analogs (D1 and D2 denote counterpart diastereoisomers)

| Triphosphate cap analog | Tetraphosphate cap analog |
|---|---|
| $m^7Gp_3G$ | $m^7Gp_4G$ |
| $m_2^{7,3'-O}Gp_3G$ | $b^7Gp_4G$ |
| $b^7Gp_3G$ | $b^7m^{3'-O}Gp_4G$ |
| $e^7Gp_3G$ | $m_2^{2,7}Gp_4G$ |
| $m_2^{2,7}Gp_3G$ | $m_3^{2,2,7}Gp_4G$ |
| $m_3^{2,2,7}Gp_3G$ | $b^7m^2Gp_4G$ |

TABLE 1-continued

Cap analogs (D1 and D2 denote counterpart diastereoisomers)

| Triphosphate cap analog | Tetraphosphate cap analog |
|---|---|
| $m^7Gp_3$2'dG | $m7Gp^4m^7G$ |
| $m^7Gp_3m^{2'\text{-}O}G$ | |
| $m^7Gp_3m^7G$ | |
| $m2^{7,2'\text{-}O}Gp_3G$ | |
| $m2^{7,2'\text{-}O}GpppsG$ (D1) | |
| $m2^{7,2'\text{-}O}GpppsG$ (D2) | |
| $m2^{7,2'\text{-}O}GppspG$ (D1) | |
| $m2^{7,2'\text{-}O}GppspG$ (D2) | |
| $m2^{7,2'\text{-}O}GpsppG$ (D1) | |
| $m2^{7,2'\text{-}O}GpsppG$ (D2) | |

Further cap analogs have been described previously (U.S. Pat. No. 7,074,596, WO 2008/016473, WO 2008/157688, WO 2009/149253, WO 2011/015347, and WO 2013/059475). The synthesis of $N^7$-(4-chlorophenoxyethyl) substituted dinucleotide cap analogs has been described recently (Kore et al., 2013. Bioorg. Med. Chem. 21(15):4570-4).

Particularly preferred cap analogs are G[5']ppp[5']G, $m^7G$[5']ppp[5']G, $m_3^{2,2,7}G$[5']ppp[5']G, $m_2^{7,3'\text{-}O}G$[5']ppp[5']G (3'-ARCA), $m_2^{7,2'\text{-}O}GpppG$ (2'-ARCA), $m_2^{7,2'\text{-}O}GppspG$ D1 (β-S-ARCA D1) and $m_2^{7,2'\text{-}O}GppspG$ D2 (β-S-ARCA D2).

Preferably the cap analog is added with an initial concentration in the range of about 1 to 20 mM, 1 to 17.5 mM, 1 to 15 mM, 1 to 12.5 mM, 1 to 10 mM, 1 to 7.5 mM, 1 to 5 mM or 1 to 2.5 mM. Even more preferred the cap analog is added with an initial concentration of about 5 to 20 mM, 7.5 to 20 mM, 10 to 20 mM or 12.5 to 20 mM.

Ribonuclease inhibitor: A ribonuclease inhibitor inhibits the action of a ribonuclease which degrades RNA. Preferably, the concentration of the ribonuclease inhibitor is from about 1 to 500 units/ml, 1 to 400 units/ml, 1 to 300 units/ml, 1 to 200 units/ml, or 1 to 100 units/ml. Even more preferred the concentration of the ribonuclease inhibitor is about 200 units/ml.

Proteinogenic amino acid: A proteinogenic amino acid is an amino acid which is incorporated into protein during translation. Proteinogenic amino acids include alanine, serine, leucine, valine, isoleucine, glycine, histidine, proline, lysine, glutamic acid, glutamine, aspartic acid, asparagine, arginine, selenocysteine, cysteine, tryptophan, methionine, phenylalanine, threonine and tyrosine.

Antioxidant: An antioxidant inhibits the oxidation of other molecules. Suitable antioxidants for use in the present invention include, but are not limited to, DTT (dithiothreitol), TCEP (tris(2-carboxyethyl)phosphine), NAC (N-acetylcysteine), beta-mercaptoethanol, glutathione, cysteine and cystine. Preferably, DTT is used in the in vitro transcription reaction.

The concentration of the antioxidant, preferably of DTT, is 1 to 50 mM, 5 to 48 mM, 8 to 47 mM, 10 to 46 mM, 15 to 45 mM, 18 to 44 mM, 20 to 43 mM, 23 to 42 mM, 25 to 41 mM or 28 to 40 mM. Preferably, the concentration is 40 mM.

Amine: Preferably, the amine to be used in the present invention is betaine (trimethylglycine). The concentration of the amine, preferably of betaine, may be 10 mM to 2M, preferably it is 0.7 M to 1.3 M.

Polyamine: Preferably, the polyamine is selected from the group consisting of spermine and spermidine. Preferably the concentration of the polyamine is from about 1 to 25 mM, 1 to 20 mM, 1 to 15 mM, 1 to 10 mM, 1 to 5 mM, or about 1 to 2.5 mM. Even more preferred the concentration of the polyamine is about 2 mM. Most preferred is a concentration of 2 mM of spermidine.

DNase: DNases are enzymes which hydrolyze DNA by catalyzing the hydrolytic cleavage of phosphodiester linkages in the DNA backbone. Suitable DNases are isolated from bovine pancreas and are available from various suppliers such as Sigma-Aldrich, New England Biolabs, Qiagen and ThermoFisher. Preferably, the used DNase is free of any RNAse activity. In the method of the present invention the treatment with DNase is performed after the RNA in vitro transcription reaction by adding the DNase to the reaction mixture used for RNA in vitro transcription. Preferably, a suitable amount of calcium chloride is added together with the DNase to the RNA in vitro transcription mixture. The suitable amount of $CaCl_2$ is from 1 to 5 mM, preferably from 2 to 4 mM and more preferably it is 3 mM. The DNA is treated with the DNase for 1 to 5 hours, preferably for 1.5 to 3 hours and more preferably for 2 hours. The DNase treatment is preferably performed at a temperature of 37° C. In one embodiment, 3 mM $CaCl_2$ and 200 U/ml DNase I are added to the RNA in vitro transcription mixture and the resulting mixture is incubated for two hours at 37° C. In another embodiment, 3 mM $CaCl_2$ and 400 U/ml DNase I are added to the RNA in vitro transcription mixture and the resulting mixture is incubated for two hours at 37° C. The DNase treatment can be stopped by adding EDTA or another chelating agent. Preferably, the DNase treatment is stopped by adding EDTA to a final concentration of 25 mM.

Bioreactor: The term bioreactor or transcription reactor as used herein refers to a chamber or test tube or column wherein an in vitro transcription reaction is carried out under specified conditions. The bioreactor may be thermally regulated to maintain accurately a specific temperature, usually between 4 and 40° C. The bioreactor may be configured with an inflow or feed line and an exit port. The bioreactor may be a stirred-cell with provision for variable rates of stirring. The bioreactor may comprise a filtration membrane for separating nucleotides and other low molecular weight components from the reaction mixture.

DETAILED DESCRIPTION OF THE INVENTION

As discussed above, the present invention is based on the finding that dicarboxylic or tricarboxylic acids reduce or prevent the formation of precipitates in a method of RNA in vitro transcription.

Hence, in a first aspect, the present invention relates to a method for in vitro transcription of a nucleic acid template into RNA, comprising the steps of:
providing a mixture comprising a dicarboxylic or tricarboxylic acid or salt thereof, a buffer substance, ribonucleoside triphosphates, one or more magnesium salts, said nucleic acid template and RNA polymerase; and
incubating the reaction mixture under suitable conditions.

The skilled person knows that the concentration of the one or more magnesium salt and the total concentration of ribonucleoside triphosphates are related to each other, meaning that a higher amount of the magnesium salt has to be present, if a higher concentration of ribonucleoside triphosphates is used in the reaction. Generally, the concentration of the magnesium salt should be slightly lower than the total concentration of ribonucleoside triphosphates. For example, if the total concentration of ribonucleoside triphosphates is 26.9 mM, the concentration of the magnesium salt may be 24 mM.

In a similar way, the concentration of the dicarboxylic or tricarboxylic acid or salt thereof, preferably of citrate, may be adjusted to the concentration of magnesium ions in the in vitro transcription reaction. Preferably, the concentration of the dicarboxylic or tricarboxylic acid or salt thereof, preferably of citrate, is at least half of the concentration of magnesium ions within the in vitro transcription reaction. For example, the concentration of the dicarboxylic or tricarboxylic acid or salt thereof, preferably of citrate, has to be at least 12 mM, if the concentration of magnesium ions is 24 mM. If a lower concentration of magnesium ions is used, the concentration of the dicarboxylic or tricarboxylic acid or salt thereof, preferably of citrate, can be reduced accordingly.

The concentration of the dicarboxylic or tricarboxylic acid or salt thereof, preferably of citrate, in the reaction mixture for in vitro transcription may be in the range of 1 mM to 100 mM, of 3 mM to 80 mM, of 5 mM to 50 mM, of 8 to 40 mM, of 10 mM to 30 mM or of 12 mM to 25 mM.

In a preferred embodiment the reaction mixture contains 12 mM of the dicarboxylic or tricarboxylic acid or salt thereof, preferably of citrate, and 24 mM of magnesium ions, preferably of magnesium chloride. In another preferred embodiment the reaction mixture contains 24 mM of a magnesium salt of a dicarboxylic or tricarboxylic acid, preferably of magnesium citrate.

The method of the present invention can be operated in the batch mode, so that all reagents of the in vitro transcription reaction are present in the reaction vessel from the beginning of the reaction and no new reagents are added and no product is removed before the in vitro transcription reaction is stopped. Alternatively, the in vitro transcription reaction may be operated in a semi-batch mode or in a continuous mode. The term semi-batch as used herein refers to the operation of the in vitro transcription reaction as a repetitive series of transcription reactions. For example, the reaction is allowed to proceed for a finite time at which point the product is removed, new reactants added, and the complete reaction repeated. The term continuous-flow as used herein refers to a reaction that is carried out continually in a bioreactor core with supplemental reactants constantly added through an input feed line and products constantly removed through an exit port.

The skilled person knows that in a reaction operated in a semi-batch mode or in a continuous mode the initial concentration of ribonucleoside triphosphates and magnesium can be lower than in the batch mode, if additional amounts of these reagents are added at some time after the start of the in vitro transcription reaction. In this case, the concentration of the dicarboxylic acid or tricarboxylic acid or salt thereof can also be lower than in the batch mode.

The total concentration of all four ribonucleoside triphosphates in the reaction mixture is 0.1 to 60 mM, 1 to 50 mM, 3 to 40 mM, 8 to 35 mM, 10 to 30 mM or 12 to 25 mM. If the in vitro transcription reaction is performed in the semi-batch or continuous mode, the initial total concentration of the four ribonucleoside triphosphates in the reaction mixture is 0.1 to 10 mM, 0.5 to 8 mM or 1 to 7 mM. In this case, the initial concentration of magnesium ions in the reaction mixture is 0.1 to 8 mM, 0.5 to 7 mM or 1 to 6 mM.

In the in vitro transcription reaction mixture the ribonucleoside triphosphates can all be present in the same amount. For example, 6 mM ATP, 6 mM UTP, 6 mM CTP and 6 mM GTP can be used in the in vitro transcription reaction mixture. Alternatively, a sequence-optimized reaction mixture can be used, wherein the fraction of each of the four ribonucleoside triphosphates within the reaction mixture corresponds to the fraction of the respective nucleotide in the RNA molecule which is to be produced by the method. Such a sequence-optimized reaction mixture is disclosed in PCT/EP2015/001164. The present invention can also be used to produce homopolymer RNAs, i.e. RNAs consisting of only one type of nucleotides. In this case, the concentration of the ribonucleoside triphosphate which forms the homopolymer is the same as the total concentration of ribonucleoside triphosphates.

The RNA produced by the in vitro transcription can be purified by any suitable method, including DNA template digest, phenol-chloroform extraction, LiCl precipitation, HPLC and/or tangential flow filtration. Preferably, the RNA is purified by HPLC using a porous reversed phase as stationary phase. Such a process is described in WO 2008/077592. Also preferably, the RNA is purified by tangential flow filtration. Such a process is described in PCT/EP2015/062002.

As discussed before, the addition of a dicarboxylic or tricarboxylic acid or salt thereof, preferably of citrate, to an in vitro transcription reaction reduces or prevents the formation of precipitates during the in vitro transcription process. The formation of precipitates can be detected spectrophotometrically by measuring the absorption of a sample taken from the in vitro transcription reaction at a wavelength of 350 to 550 nm, preferably at a wavelength of 500. The absorption at 500 nm increases when precipitates form. A suitable apparatus for detecting the precipitates is Nanodrop 2000 UV spectrophotometer. Alternatively, the precipitates can be separated from the soluble compounds and then be analyzed, for example by centrifugation, size exclusion chromatography, dynamic or static light scattering, automated particle sorting or ultracentrifuge fractionation.

The addition of a dicarboxylic or tricarboxylic acid or salt thereof, preferably of citrate, to an in vitro transcription reaction reduces the formation of precipitates during the in vitro transcription process compared to an in vitro transcription reaction with the same reaction mixture which does not contain said dicarboxylic or tricarboxylic acid or salt thereof by at least 10% or 20%, preferably by at least 30%, 40% or 50%, more preferably by at least 60%, 70% or 80%, even more preferably by at least 90%, 95% or 98% and most preferably no precipitates can be detected in an in vitro transcription reaction containing said dicarboxylic or tricarboxylic acid or salt thereof.

In another aspect, the present invention relates to the use of an amine, preferably of betaine, in the RNA in vitro transcription of a nucleic acid template with a high percentage of guanosine and cytosine nucleotides.

A betaine is a neutral chemical compound with a positively charged cationic functional group such as a quaternary ammonium or phosphonium cation which bears no hydrogen atom and with a negatively charged functional group such as a carboxylate group which may not be adjacent to the cationic site. Preferably, the betaine is trimethylglycine, i.e. the amino acid glycine which has three methyl groups bound to the nitrogen atom of the amino acid.

A nucleic acid template is considered to have a high percentage of guanosine and cytosine nucleotides, if the number of guanosine and cytosine nucleotides is at least 50%, preferably at least 55% and more preferably at least 60% of the total number of nucleotides within a nucleic acid template. The high percentage of guanosine and cytosine nucleotides may be present in the complete nucleic acid template or a part thereof which has a length of at least 10% or 20%, preferably of at least 30% or 40%, more preferably of at least 50% or 60% and even more preferably of at least 70% or 80% of the total length of the nucleic acid template.

Without wishing to be bound by the theory, it is hypothesized that the use of betaine, preferably of trimethylglycine, in the RNA in vitro transcription of a nucleic acid template with a high percentage of guanosine and cytosine nucleotides reduces the formation of secondary structures which may reduce the transcription efficiency.

Accordingly, the present invention also relates to the use of betaine, preferably of trimethylglycine, in the reduction of secondary structures in a nucleic acid template for RNA in vitro transcription having a high percentage of guanosine and cytosine nucleotides.

EXAMPLES

The following examples are intended to illustrate the invention in a further way. They are merely illustrative and not intended to limit the subject matter of the invention.

Example 1: Preparation of DNA and mRNA Constructs

For the present examples, a DNA sequence encoding *Photinus pyralis* luciferase (PpLuc) was prepared by modifying the wild type encoding PpLuc DNA sequence by GC-optimization for stabilization (SEQ ID NO: 1). The GC-optimized PpLuc DNA sequence was introduced into a pUC 19 derived vector and modified to comprise a alpha-globin-3'-UTR (muag (mutated alpha-globin-3'-UTR)), a histone-stem-loop structure, and a stretch of 70× adenosine at the 3'-terminal end (poly-A-tail). The obtained plasmid DNA was used for RNA in vitro transcription experiments (see Example 4 and 5) to obtain PpLuc RNA (SEQ ID NO: 2).

Example 2: Characterization of Precipitates Formed During RNA In Vitro Transcription Using a State-of-the-Art HEPES-KOH Buffer The goal of that experiment was to characterize the composition of precipitates that are formed during RNA in vitro transcription.

RNA In Vitro Transcription and Analysis of Precipitates:

The RNA in vitro transcription reaction was performed using a linear DNA template as described in Example 1. The reaction mixture also contained 24 mM $MgCl_2$, 13.45 mM NTP mixture, 16.1 mM Cap analog and 2500 units/ml T7 RNA Polymerase. As buffer system HEPES-KOH pH 8.0 was used. At certain time points of the transcription reaction, samples were taken (0 h, 1 h, 2 h, 3 h, 4 h). Both precipitates that accumulated in the reaction tube and the supernatant of the reaction were further analyzed on a conventional SDS-polyacrylamide gel. The result of this analysis is shown in FIG. 1.

Results:

The results show that the precipitates formed during RNA in vitro transcription (reaction buffer HEPES-KOH) contain RNA and proteins.

Example 3: Preparation of RNA In Vitro Transcription Buffers

In the following, the preparation of the conventional RNA in vitro transcription buffers (HEPES and Tris-HCl) and RNA in vitro transcription buffers comprising citrate or acetate is described.

Preparation of the HEPES Buffer:

First, a 5× stock HEPES buffer was prepared, comprising 400 mM HEPES, 10 mM spermidine, 200 mM DTT and 25 units/ml pyrophosphatase. The pH of the buffer was set to 7.5, using KOH. The HEPES buffer was used in 1× concentration in the RNA in vitro transcription experiment (see Example 4).

Preparation of Tris Buffers:

First, a 5× stock TRIS buffer was prepared, comprising 400 mM Tris, 10 mM spermidine, 200 mM DTT and 25 units/ml pyrophosphatase. To prepare a Tris-HCl buffer pH 7.5, the titration of the pH was done with HCl. To prepare a Tris-acetate buffer pH 7.5, the titration of the pH was done with acetic acid. To prepare a Tris-citrate buffer pH 7.5, the titration of the pH was done with 4 M citric acid. In addition, all prepared TRIS buffers also contained 25 mM KOH. KOH was added to enable a better comparability of the obtained results, because the HEPES buffer also contained KOH (see Example 4). The Tris buffers (Tris-HCl buffer pH 7.5, Tris-acetate buffer pH 7.5, Tris-citrate buffer pH 7.5) were used in 1× concentration in the RNA in vitro transcription experiment (see Example 4).

Example 4: RNA In Vitro Transcription Using Different Buffer Systems

The goal of this experiment was to characterize the effect of different RNA in vitro transcription buffers on the formation of precipitates. In that experiment, buffers known in the art (HEPES, Tris-HCl) and buffers comprising acetate or citrate (Tris-Acetate, Tris-Citrate) were tested. The RNA in vitro transcription reaction was performed over 90 minutes, and three different samples taken at 30 minutes, 60 minutes and 90 minutes were analyzed spectrometrically (absorption at 500 nm) to detect precipitates.

RNA In Vitro Transcription Reaction:

The RNA in vitro transcription reaction was performed using a linear DNA template as described in Example 1. The reaction mixture also contained 24 mM $MgCl_2$, 13.45 mM NTP mixture, 16.1 mM Cap analog and 2500 units/ml T7 RNA Polymerase. As buffer systems, either HEPES-KOH pH 7.5, Tris-HCl pH 7.5, Tris-acetate pH 7.5, or Tris-citrate pH 7.5 were used (prepared according to Example 3). Samples of the respective reactions were taken at 0 minutes, 30 minutes, 60 minutes and 90 minutes to monitor the formation of precipitations.

Figure 2:
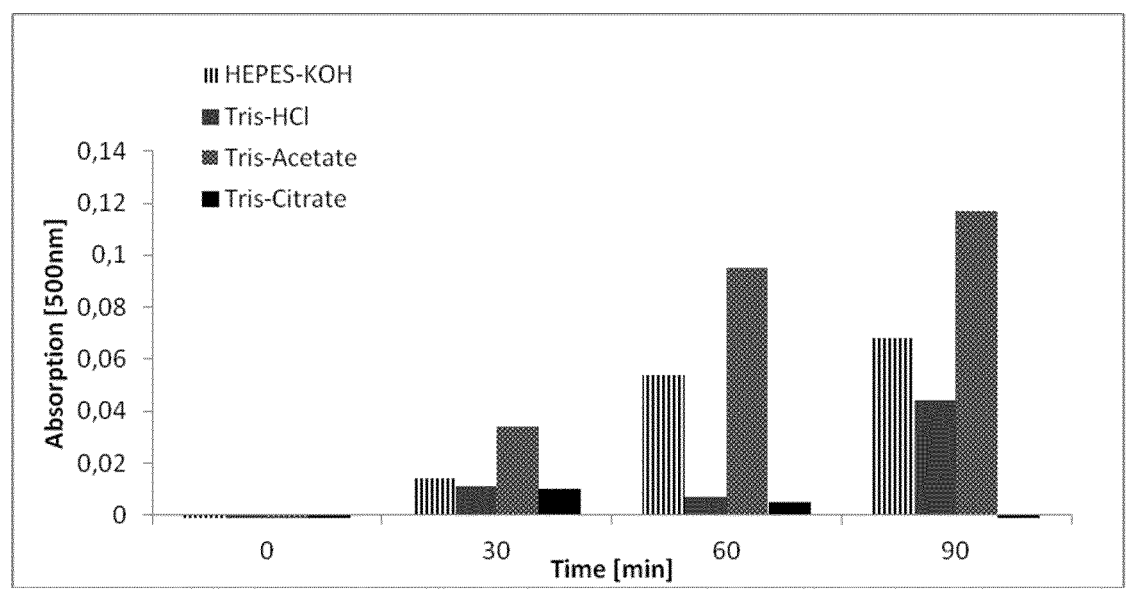
FIG. 2 shows an analysis of precipitate formation during RNA in vitro transcription reaction, testing the Tris-citrate buffer according to the present invention in comparison to Tris-acetate buffer and buffers known in the art (HEPES, Tris-HCl). The formation of precipitates was measured over time, using light spectrometry (absorption at 500 nm). For a detailed description of the experiment see Example 4.

Spectrometric Detection of Precipitates Formed During the RNA In Vitro Transcription:

The samples obtained during the RNA in vitro transcription reactions were spectrometrically analyzed (Nanodrop 2000 UV-spectrometer). The absorption of at a wavelength of 500 nm is a measure to determine the presence of precipitates. The results of the measurements are shown in FIG. 2.

Results:

The results show that the use of a Tris buffer prepared with the monocarboxylic acid acetic acid (Tris-acetate buffer pH 7.5) led to the formation of more precipitates during RNA in vitro transcription compared to the state-of-the-art buffers HEPES and Tris-HCl. However, the results surprisingly show that the Tris-buffer prepared with citric acid (Tris-citrate, pH 7.5) completely blocked the formation of precipitates (see FIG. 2).

Example 5: RNA In Vitro Transcription Using Tris Buffers with Different Citrate Concentrations The goal of this experiment was to characterize the effect of citrate observed in Example 4 in more detail. Therefore, buffers with different citrate concentrations ranging from 0 mM citrate to 25 mM citrate were prepared, and the effect on precipitate formation was analyzed. The RNA in vitro transcription reaction was performed over 70 minutes, and two different samples taken at 30 minutes and 70 minutes were spectrometrically analyzed (absorption at 500 nm) to detect precipitates.

Figure 3:
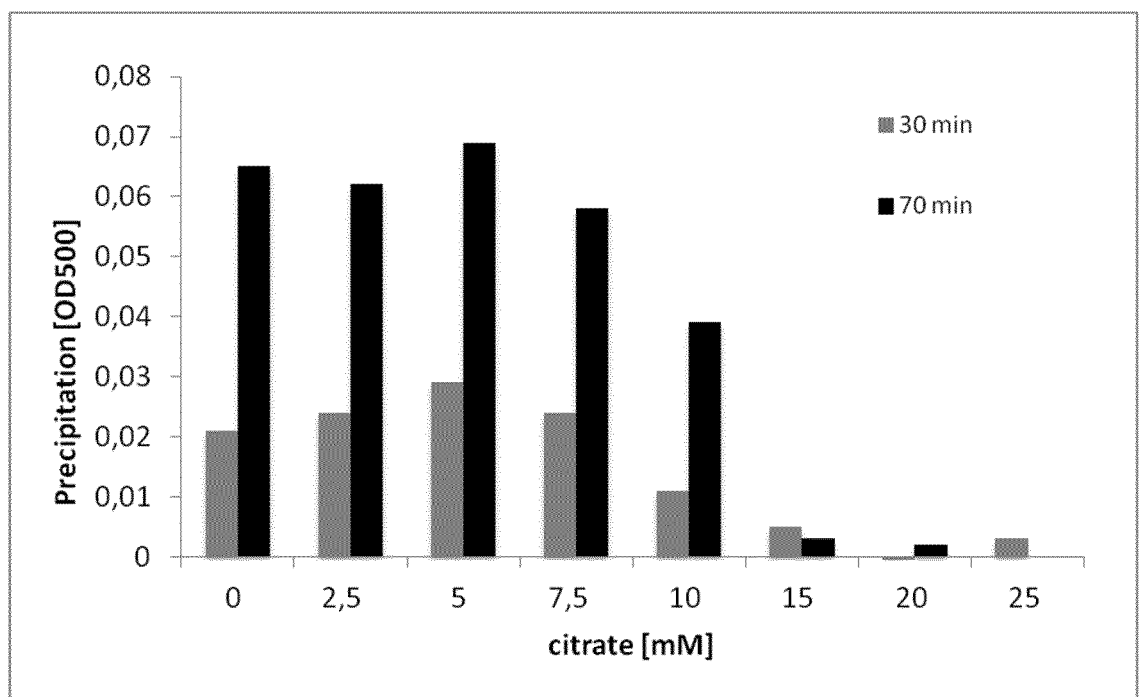
FIG. 3 shows an analysis of precipitate formation during RNA in vitro transcription reaction, testing different citrate concentrations, ranging from 0 mM to 25 mM, in a Tris buffer system at pH 8.0. For a detailed description of the experiment, see Example 5.

RNA In Vitro Transcription Reaction and Detection of Precipitates:

The RNA in vitro transcription reaction mixture was prepared as described in Example 4. The RNA in vitro transcription reaction was performed in eight different Tris-HCl buffers (pH 7.95) containing different concentrations of citrate (0 mM-25 mM sodium citrate). At 30 minutes and 70 minutes, samples were taken and spectrometrically analyzed (according to Example 4). The results of the experiment are shown in FIG. 3.

Results:

The results show that the reduction of precipitations was a dose-dependent effect of citrate. Moreover, the experiment showed that at citrate concentrations >10 mM, the formation of precipitates was already strongly reduced, and at concentrations >15 mM, the formation of precipitates could be completely prevented (see FIG. 3).

Example 6: RNA In Vitro Transcription Using HEPES Buffers with Different Citrate Concentrations The goal of this experiment was to evaluate if the observed effect of citrate on the prevention of precipitates in Tris buffer is also transferrable to other buffers such as HEPES.

Figure 4:
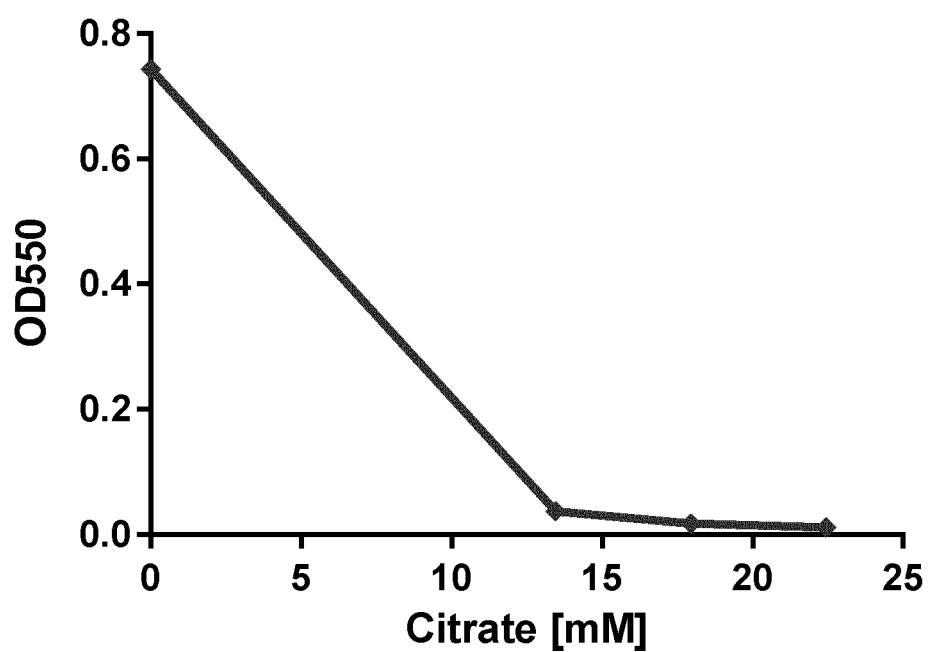
FIG. 4 shows an analysis of precipitate formation during RNA in vitro transcription reaction, testing different citrate concentrations, ranging from 0 mM to 25 mM, in a HEPES buffer system at pH 8.0 after 120 minutes RNA in vitro transcription. For a detailed description of the experiment, see Example 6.

Therefore, HEPES-KOH buffers pH 8.0 with different citrate concentrations ranging from 0 mM citrate to 22.45 mM citrate (i.e. 0 mM; 13.45 mM; 17.95 mM; 22.45 mM citrate) were prepared, and the effect on precipitate formation was analyzed. The RNA in vitro transcription reaction was performed over 120 minutes, and samples for each buffer condition were taken at 120 minutes and analyzed spectrometrically (absorption at 550 nm) to detect precipitates. The results are shown in FIG. 4.

Results:

The results show that the reduction of precipitations in a HEPES-buffered reaction was a dose-dependent effect of citrate. Moreover, the experiment showed that at citrate concentrations >10 mM, the formation of precipitates was already strongly reduced, and at concentrations >15 mM, the formation of precipitates could be completely prevented (see FIG. 4).

Example 7: DNA Hydrolysis after RNA In Vitro Transcription

The goal of this experiment was to evaluate whether the observed positive effect on the prevention of precipitates also improves and optimizes the hydrolysis of the DNA template after RNA in vitro transcription. DNA template is conventionally hydrolyzed using DNAses, enzymes that need $Ca^{2+}$ ions and $Mg^{2+}$ ions to be active and efficient. An ideal RNA in vitro transcription buffer should promote the function of DNAses to hydrolyze DNA template, eventually preventing DNA contaminations of the final RNA product.

DNA Digestion of the Template:

RNA in vitro transcription was essentially performed according to Example 1, using four different buffer systems (Tris-HCl; Tris-HCl+6 mM Citrate; Tris-HCl+10 mM Citrate; HEPES-KOH+10 mM Citrate).

In a first set of experiments, DNA template was removed by adding 3 mM $CaCl_2$ and 200 U/ml DNAse1 (Thermo Fisher) and incubating for 2 h at 37° C. The digestion reaction was stopped by adding EDTA to a final concentration of 25 mM.

In a second set of experiments, DNA template was removed by adding 3 mM $CaCl_2$ and 400 U/ml DNAse1 (Thermo Fisher) and incubating for 2 h at 37° C. The digestion reaction was stopped by adding EDTA to a final concentration of 25 mM.

Analysis of Residual pDNA Using qPCR:

A qPCR method was used to detect residual pDNA using specific primers and probes for the origin of replication of the pDNA. Quantitative PCR was performed using a LightCycler and LightCycler Master Mix (Roche Diagnostics) according to the manufacturer's instructions. The results of the analysis are shown in FIG. 5.

Figure 5:
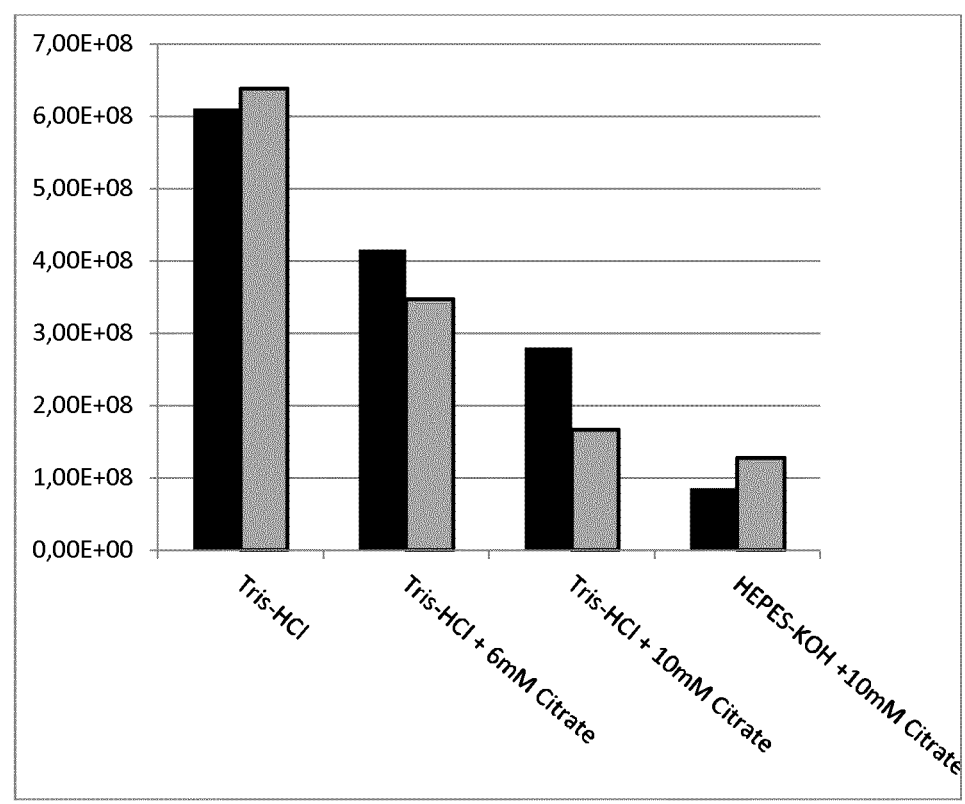
FIG. 5 shows a qPCR analysis of residual pDNA template present in the RNA after DNA hydrolysis. Buffer conditions of the DNAse treatment are indicated. Black columns: 3 mM CaCl2 and 200 U/ml DNAse1; Grey columns: 3 mM CaCl2 and 400/ml DNAse1. The copy number of pDNA in the RNA is expressed as copies/µg RNA. For a detailed description of the experiment, see Example 7.

Results:

The results show that the inventive RNA in vitro transcription buffer system comprising citrate promotes the hydrolysis of the DNA template by DNase (see FIG. 5).

The inventive buffer system is therefore suitable to produce RNA with reduced DNA contaminations. Moreover, the more efficient DNA hydrolysis may also economize the industrial RNA production process, as less DNAse enzyme is needed to digest pDNA template.

The invention claimed is:

1. A method for in vitro transcription of a DNA template into RNA, comprising the steps of:
   providing a mixture comprising: citric acid, or a citric acid salt, in a concentration of 10 to 100 mM, a buffer substance, ribonucleoside triphosphates, one or more magnesium salts, said DNA template and a recombinant RNA polymerase, wherein the mixture does not comprise a proteinogenic amino acid or tRNA; and
   incubating the reaction mixture under suitable conditions thereby producing the RNA.

2. A method for preparing RNA, comprising the steps of:
   a) incubating a mixture comprising: citric acid, or a citric acid salt, in a concentration of 10 to 100 mM, a buffer substance, ribonucleoside triphosphates, one or more magnesium salts, a nucleic acid template and a recombinant RNA polymerase under suitable conditions;
   b) adding a DNase to the mixture of a) and incubating the resulting mixture containing DNase under suitable conditions thereby producing the RNA.

3. The method of claim 1, wherein the citric acid or citric acid salt comprises sodium citrate and/or Tris-citrate.

4. The method according to claim 3, wherein the concentration of citric acid or citric acid salt is at least half of the concentration of magnesium ions present in the in vitro transcription reaction.

5. The method of claim 1, wherein the buffer substance is Tris base, HEPES or Tris-HCl.

6. The method of claim 1, wherein the concentration of the buffer substance is 10 to 100 mM.

7. The method of claim 1, wherein the reaction mixture comprises Tris-citrate or HEPES-KOH plus sodium citrate, ribonucleoside triphosphates, one or more magnesium salts, said DNA template and RNA polymerase.

8. The method of claim 1, wherein the magnesium salt is magnesium chloride.

9. The method according to claim 8, wherein the concentration of magnesium chloride is 1 to 100 mM.

10. The method of claim 1, wherein the reaction mixture has a pH of 6 to 8.5.

11. The method of claim 1, wherein the RNA polymerase is T7 RNA polymerase.

12. The method of claim 1, wherein the total concentration of ribonucleoside triphosphates in the mixture is between 0.1 and 60 mM.

13. The method of claim 1, wherein the DNA template is a linearized plasmid DNA template.

14. The method of claim 1, wherein the reaction mixture further comprises one or more of ribonuclease inhibitor, pyrophosphatase, cap analog, one or more antioxidants and one or more amines and/or polyamines.

15. The method according to claim 14, wherein the antioxidant is DTT.

16. The method of claim 14, wherein the polyamine is spermidine.

17. The method of claim 1, further comprising a step (c) of purifying the RNA.

18. The method according to claim 17, wherein the step of purifying the RNA comprises HPLC using a porous reversed phase as stationary phase and/or tangential flow filtration.

19. A reaction mixture comprising: citric acid, or a citric acid salt, in a concentration of 10 to 100 mM, a buffer substance, ribonucleoside triphosphates, a cap analog, one or more magnesium salts, a DNA template, a RNA molecule comprising a 5' cap and a recombinant RNA polymerase, but not comprising a proteinogenic amino acid or tRNA, said RNA molecule comprising a heterologous 3'-UTR that comprises a Poly(A) sequence.

20. A method for the reduction of the formation of precipitates in a method of in vitro transcription, the method comprising
providing a mixture comprising: citric acid, or a citric acid salt, in a concentration of 10 to 100 mM, a buffer substance, ribonucleoside triphosphates, one or more magnesium salts, a DNA template and a recombinant RNA polymerase, wherein the mixture does not comprise a proteinogenic amino acid or tRNA; and
incubating the reaction mixture under suitable conditions thereby producing a RNA composition having a reduced amount of precipitates as compared to a method not including said citric acid or citric acid salt.

21. The method of claim 3, wherein the mixture comprises 10 to 100 mM of sodium citrate.

22. The method of claim 14, wherein the RNA comprises a 5' Cap, a 5'-UTR, an open reading frame, a 3'-UTR and a poly(A) sequence.

23. The reaction mixture of claim 19, wherein the RNA molecule comprises at least one nucleotide analog.

24. The reaction mixture of claim 23, wherein the heterologous 3' UTR comprises an alpha-globin 3'-UTR.

25. The method of claim 1, wherein the RNA comprises at least one nucleotide analog.

26. The method of claim 25, wherein the at least one nucleotide analog is selected from the group consisting of pseudouridine, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

27. The method of claim 26, wherein the at least one nucleotide analog is pseudouridine or 1-methyl-pseudouridine.

28. The reaction mixture of claim 23, wherein the at least one nucleotide analog is selected from the group consisting of pseudouridine, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

29. The reaction mixture of claim 28, wherein the at least one nucleotide analog is pseudouridine or 1-methyl-pseudouridine.

* * * * *

SEQUENCE LISTING

```
<160> NUMBER OF SEQ ID NOS: 2

<210> SEQ ID NO 1
<211> LENGTH: 1653
<212> TYPE: DNA
<213> ORGANISM: artificial
<220> FEATURE:
<223> OTHER INFORMATION: Pp luc DNA

<400> SEQUENCE: 1
atggaggacg ccaagaacat caagaagggc ccggcgccct tctacccgct ggaggacggg      60
accgccggcg agcagctcca caaggccatg aagcggtacg ccctggtgcc gggcacgatc     120
gccttcaccg acgcccacat cgaggtcgac atcacctacg cggagtactt cgagatgagc     180
gtgcgcctgg ccgaggccat gaagcggtac ggcctgaaca ccaaccaccg gatcgtggtg     240
```

```
tgctcggaga acagcctgca gttcttcatg ccggtgctgg gcgccctctt catcggcgtg      300
gccgtcgccc cggcgaacga catctacaac gagcgggagc tgctgaacag catggggatc      360
agccagccga ccgtggtgtt cgtgagcaag aagggcctgc agaagatcct gaacgtgcag      420
aagaagctgc ccatcatcca gaagatcatc atcatggaca gcaagaccga ctaccagggc      480
ttccagtcga tgtacacgtt cgtgaccagc cacctcccgc cgggcttcaa cgagtacgac      540
ttcgtcccgg agagcttcga ccgggacaag accatcgccc tgatcatgaa cagcagcggc      600
agcaccggcc tgccgaaggg ggtggccctg ccgcaccgga ccgcctgcgt gcgcttctcg      660
cacgcccggg accccatctt cggcaaccag atcatcccgg acaccgccat cctgagcgtg      720
gtgccgttcc accacggctt cggcatgttc acgaccctgg gctacctcat ctgcggcttc      780
cgggtggtcc tgatgtaccg gttcgaggag gagctgttcc tgcggagcct gcaggactac      840
aagatccaga gcgcgctgct cgtgccgacc ctgttcagct tcttcgccaa gagcaccctg      900
atcgacaagt acgacctgtc gaacctgcac gagatcgcca gcgggggcgc cccgctgagc      960
aaggaggtgg gcgaggccgt ggccaagcgg ttccacctcc cgggcatccg ccagggctac     1020
ggcctgaccg agaccacgag cgcgatcctg atcaccccg aggggggacga caagccgggc     1080 gccgtgggca aggtggtccc gttcttcgag gccaaggtgg tggacctgga caccggcaag     1140
accctgggcg tgaaccagcg gggcgagctg tgcgtgcggg gccgatgat catgagcggc      1200 tacgtgaaca cccggaggc caccaacgcc ctcatcgaca aggacggctg gctgcacagc      1260
ggcgacatcg cctactggga cgaggacgag cacttcttca tcgtcgaccg gctgaagtcg      1320
ctgatcaagt acaaggggta ccaggtggcg ccggccgagc tggagagcat cctgctccag      1380
caccccaaca tcttcgacgc cggcgtggcc gggctgccgg acgacgacgc cggcgagctg      1440
ccggccgcgg tggtggtgct ggagcacggc aagaccatga cggagaagga gatcgtcgac      1500
tacgtggcca gccaggtgac caccgccaag aagctgcggg gcggcgtggt gttcgtggac      1560
gaggtcccga gggcctgac cgggaagctc gacgcccgga gatccgcga gatcctgatc      1620 aaggccaaga agggcggcaa gatcgccgtg tga                                   1653

```

<210> SEQ ID NO 2
<211> LENGTH: 1870
<212> TYPE: RNA
<213> ORGANISM: artificial
<220> FEATURE:
<223> OTHER INFORMATION: PpLuc RNA

<400> SEQUENCE: 2

```
gggagaaagc uuaccaugga ggacgccaag aacaucaaga agggcccggc gcccuucuac       60
ccgcuggagg acgggaccgc cggcgagcag cuccacaagg ccaugaagcg guacgcccug      120
gugccgggca cgaucgccuu caccgacgcc cacaucgagg ucgacaucac cuacgcggag      180
uacuucgaga ugagcgugcg ccuggccgag gccaugaagc gguacggccu gaacaccaac      240
caccggaucg uggugugcuc ggagaacagc cugcaguucu ucaugccggu gcugggcgcc      300
cucuucaucg gcguggccgu cgccccggcg aacgacaucu acaacgagcg ggagcugcug      360
aacagcaugg gaucagcca gccgaccgug guguucguga gcaagaaggg ccugcagaag      420
auccugaacg ugcagaagaa gcugcccauc auccagaaga ucaucaucau ggacagcaag      480
accgacuacc agggcuucca gucgauguac acguucguga ccagccaccu cccgccgggc      540
uucaacgagu acgacuucgu cccggagagc uucgaccggg acaagaccau cgcccugauc      600
augaacagca gcggcagcac cggccugccg aaggggugg cccugccgca ccggaccgcc      660
```

```
ugcgugcgcu ucucgcacgc ccgggacccc aucuucggca accagaucau cccggacacc     720
gccauccuga gcguggugcc guuccaccac ggcuucggca uguucacgac ccugggcuac     780
cucaucugcg gcuuccgggu gguccugaug uaccgguucg aggaggagcu guuccugcgg     840
agccugcagg acuacaagau ccagagcgcg cugcucgugc cgacccuguu cagcuucuuc     900
gccaagagca cccugaucga caaguacgac cugucgaacc ugcacgagau cgccagcggg     960
ggcgccccgc ugagcaagga ggugggcgag gccguggcca agcgguucca ccucccgggc    1020
auccgccagg gcuacggccu gaccgagacc acgagcgcga uccugaucac ccccgagggg    1080
gacgacaagc cgggcgccgu gggcaaggug gucccguucu ucgaggccaa ggugguggac    1140
cuggacaccg gcaagacccu gggcgugaac cagcggggcg agcugugcgu gcggggccg     1200 augaucauga gcggcuacgu gaacaacccg gaggccacca acgcccucau cgacaaggac    1260
ggcuggcugc acagcggcga caucgccuac ugggacgagg acgagcacuu cuucaucguc    1320
gaccggcuga agucgcugau caaguacaag ggcuaccagg uggcgccggc cgagcuggag    1380
agcauccugc uccagcaccc caacaucuuc gacgccggcg uggccgggcu gccggacgac    1440
gacgccggcg agcugccggc cgcgguggug gugcuggagc acggcaagac caugacggag    1500
aaggagaucu ucgacuacgu ggccagccag gugaccaccg ccaagaagcu gcggggcggc    1560
gugguguucg uggacgaggu cccgaagggc cugaccggga agcucgacgc ccggaagauc    1620
cgcgagaucc ugaucaaggc caagaagggc ggcaagaucg ccgugugagg acuaguuaua    1680
agacugacua gcccgauggg ccucccaacg ggcccuccuc cccuccuugc accgagauua    1740
auaaaaaaaa aaaaaaaaaa aaaaaaaaaa aaaaaaaaaa aaaaaaaaaa aaaaaaaaaa    1800
aaaaaaugca ucccccccc ccccccccc ccccccccc ccaaaggcuc uuuucagagc       1860
caccagaauu                                                           1870
```